(12) United States Patent
Clark et al.

(10) Patent No.: US 10,088,398 B2
(45) Date of Patent: Oct. 2, 2018

(54) STIRRED CELL AND METHOD OF USING SAME

(71) Applicant: EMD Millipore Corporation, Burlington, MA (US)

(72) Inventors: Phillip Clark, Wakefield, MA (US); Kurt Greenizen, Atkinson, NH (US); John Doyle, Kensington, NH (US)

(73) Assignee: EMD Millipore Corporation, Burlington, MA (US)

( * ) Notice: Subject to any disclaimer, the term of this patent is extended or adjusted under 35 U.S.C. 154(b) by 80 days.

(21) Appl. No.: 14/994,402

(22) Filed: Jan. 13, 2016

(65) Prior Publication Data

US 2016/0228870 A1 Aug. 11, 2016

Related U.S. Application Data (60) Provisional application No. 62/114,761, filed on Feb. 11, 2015.

(51) Int. Cl.
*G01N 1/40* (2006.01)
*B01L 3/00* (2006.01)

(52) U.S. Cl.
CPC ............ *G01N 1/4005* (2013.01); *B01L 3/502* (2013.01); *B01L 2200/026* (2013.01);
(Continued)

(58) Field of Classification Search
CPC .................. G01N 1/4005; B01L 3/502; B01L 2400/0633; B01L 2400/0605;
(Continued)

(56) References Cited

U.S. PATENT DOCUMENTS 3,539,155 A 11/1970 Agranat
3,807,396 A 4/1974 Fischel
(Continued)

FOREIGN PATENT DOCUMENTS

CN 2160308 Y 4/1994
CN 2329280 Y 7/1999
(Continued)

OTHER PUBLICATIONS

European communication dated Jun. 13, 2016 in corresponding European patent application No. 16155180.9.
(Continued)

*Primary Examiner* — Lore R Jarrett
(74) *Attorney, Agent, or Firm* — Nields, Lemack & Frame, LLC (57) ABSTRACT

Fluid containment pressure vessel that eliminates the outer support housing present in certain conventional vessels, and provides an improved cap-to-body interface. In certain embodiments, the cap is threaded and configured to threadingly engage with the body of the pressure vessel, and has sufficient structural integrity to withstand the pressures in the device without the need for a support housing. In certain embodiments, an interlock mechanism is provided that prevents the cap from being opened (e.g., removed from the body) while the device is under pressure. In certain embodiments, a pressure relief valve is provided with a pre-loaded biasing mechanism to achieve the required pressure release rate. The vessel can be used for sample preparation, including purification or concentration of samples, particularly protein samples.

11 Claims, 10 Drawing Sheets

(52) U.S. Cl.
CPC . *B01L 2200/0689* (2013.01); *B01L 2200/085* (2013.01); *B01L 2200/087* (2013.01); *B01L 2300/042* (2013.01); *B01L 2300/048* (2013.01); *B01L 2300/049* (2013.01); *B01L 2300/0681* (2013.01); *B01L 2300/14* (2013.01); *B01L 2400/0487* (2013.01); *B01L 2400/0605* (2013.01); *B01L 2400/065* (2013.01); *B01L 2400/0633* (2013.01)

(58) Field of Classification Search
CPC ....... B01L 2400/0487; B01L 2200/085; B01L 2200/026; B01L 2400/065; B01L 2200/087; B01L 2300/048; B01L 2300/14; B01L 2300/049; B01L 2300/042; B01L 2300/0681; B01L 2200/0689; B01F 3/04794; B01F 2003/049; A23L 2/54; A47J 31/46; A23V 2002/00
See application file for complete search history.

(56) References Cited

U.S. PATENT DOCUMENTS

| | | | |
|---|---|---|---|
| 3,868,965 A | 3/1975 | Noiles et al. | |
| 3,965,900 A | 6/1976 | Boedecker | |
| 4,082,668 A | 4/1978 | Zeineh et al. | |
| D251,681 S | 4/1979 | Lawler | |
| 4,190,426 A | 2/1980 | Ruschke | |
| D263,504 S | 3/1982 | Fowles | |
| 4,452,372 A | 6/1984 | Robbins | |
| 4,599,170 A | 7/1986 | Friedman et al. | |
| 4,784,654 A | 11/1988 | Beecher | |
| 4,930,997 A | 6/1990 | Bennett | |
| 4,932,550 A | 6/1990 | Moucha | |
| 5,087,250 A | 2/1992 | Lichte et al. | |
| 5,148,938 A | 9/1992 | Morgan | |
| 5,637,104 A | 6/1997 | Ball et al. | |
| 5,645,540 A | 7/1997 | Henniges et al. | |
| 5,881,926 A | 3/1999 | Ross | |
| D420,744 S | 2/2000 | Ostgaard et al. | |
| 6,358,232 B1 | 3/2002 | Hand et al. | |
| 6,443,978 B1 | 9/2002 | Zharov | |
| D510,769 S | 10/2005 | Bublewitz et al. | |
| 7,395,755 B1 | 7/2008 | Deese | |
| D690,826 S | 10/2013 | Kuroda et al. | |
| 8,991,418 B2 | 3/2015 | Lin | |
| D731,672 S | 6/2015 | Kuroda et al. | |
| D735,880 S | 8/2015 | Bargh et al. | |
| 2004/0020368 A1 | 2/2004 | Cai | |
| 2009/0264837 A1 | 10/2009 | Adahan | |
| 2009/0301601 A1 | 12/2009 | Enerson et al. | |
| 2009/0311776 A1* | 12/2009 | Kelly, Jr. | C12M 23/20 435/289.1 |
| 2010/0044379 A1* | 2/2010 | Asterlin | F16J 13/22 220/324 |
| 2011/0081643 A1* | 4/2011 | Fournier-Bidoz | B01F 13/0827 435/5 |
| 2013/0315780 A1 | 11/2013 | Cook et al. | |
| 2014/0165984 A1 | 6/2014 | Colby | |
| 2014/0166439 A1 | 6/2014 | Hughes | |
| 2014/0209538 A1 | 7/2014 | Nahmani et al. | |
| 2014/0224770 A1 | 8/2014 | Hensberger et al. | |
| 2014/0231442 A1 | 8/2014 | Hill et al. | |
| 2014/0284913 A1 | 9/2014 | Diehl et al. | |
| 2014/0299536 A1 | 10/2014 | Baba | |
| 2014/0339223 A1 | 11/2014 | Backaert et al. | |
| 2015/0090339 A1 | 4/2015 | Spexarth et al. | |

FOREIGN PATENT DOCUMENTS

| | | |
|---|---|---|
| CN | 201236947 Y | 5/2009 |
| CN | 203098988 U | 7/2013 |
| CN | 103759136 A | 4/2014 |
| CN | 203515652 U | 4/2014 |
| CN | 203560190 U | 4/2014 |
| CN | 203641606 U | 6/2014 |
| CN | 203670939 U | 6/2014 |
| CN | 103940290 A | 7/2014 |
| CN | 203680125 U | 7/2014 |
| CN | 203742648 U | 7/2014 |
| CN | 103965396 A | 8/2014 |
| CN | 103979489 A | 8/2014 |
| CN | 104003391 A | 8/2014 |
| CN | 104051966 A | 9/2014 |
| CN | 104056584 A | 9/2014 |
| CN | 203809033 U | 9/2014 |
| CN | 203836316 U | 9/2014 |
| CN | 203925571 U | 11/2014 |
| CN | 203926765 U | 11/2014 |
| CN | 104235586 A | 12/2014 |
| CN | 204061366 U | 12/2014 |
| CN | 204096239 U | 1/2015 |
| CN | 204115048 U | 1/2015 |
| CN | 204174183 U | 2/2015 |
| CN | 204178907 U | 2/2015 |
| CN | 204225842 U | 3/2015 |
| CN | 1474/CHE/2015 A | 4/2015 |
| CN | 104571171 A | 4/2015 |
| CN | 104594452 A | 5/2015 |
| CN | 204319475 U | 5/2015 |
| CN | 204325755 U | 5/2015 |
| CN | 204340819 U | 5/2015 |
| CN | 204345009 U | 5/2015 |
| CN | 204348664 U | 5/2015 |
| CN | 204378994 U | 6/2015 |
| CN | 204416587 U | 6/2015 |
| CN | 204465091 U | 7/2015 |
| CN | 204468915 U | 7/2015 |
| CN | 204474360 U | 7/2015 |
| CN | 204476682 U | 7/2015 |
| CN | 204514387 U | 7/2015 |
| DE | 3341600 A1 | 5/1984 |
| DE | 8337223 U1 | 9/1984 |
| DE | 3445446 A1 | 7/1985 |
| DE | 3407787 A1 | 9/1985 |
| DE | 3807188 A1 | 11/1988 |
| DE | 102014000616 A1 | 7/2015 |
| EP | 0359995 A2 | 3/1990 |
| GB | 186605 A | 1/1923 |
| GB | 786872 A | 11/1957 |
| GB | 1283273 A | 7/1972 |
| GB | 2516252 A | 1/2015 |
| JP | 51-24670 U | 2/1976 |
| JP | 53-7365 U | 1/1978 |
| JP | 53-135149 U | 10/1978 |
| JP | 57-66716 A | 4/1982 |
| JP | 2007-303553 A | 11/2007 |
| JP | 2014-226556 A | 12/2014 |
| KR | 101429592 B1 | 8/2014 |
| WO | 2008/079109 A1 | 7/2008 |
| WO | 2015/036137 A2 | 3/2015 |
| WO | 2015/109639 A1 | 7/2015 |

OTHER PUBLICATIONS

"Stirred Ultrafiltration Cells" User Guide, Millipore, Oct. 2004.
Notice of allowance dated Sep. 8, 2017 in co-pending U.S. Appl. No. 29/530,023.
Chinese communication, with English translation, dated Jan. 2, 2018 in corresponding Chinese patent application No. 201610085682.X.
Japanese communication, with English translation, dated Jan. 9, 2018 in corresponding Japanese patent application No. 2016-024045.
Japanese communication, with English translation, dated Feb. 28, 2017 in corresponding Japanese patent application No. 2016-024045.
IP.com Prior Art Database Technical Disclosure, "A Remote Fuel Tank Depressurization Method for PHEV Vehicles", IP.com No. 000241445, Apr. 28, 2015.

(56) References Cited

OTHER PUBLICATIONS

Office action dated Jun. 20, 2016 in co-pending U.S. Appl. No. 29/530,023.
Final rejection dated Feb. 14, 2017 in co-pending U.S. Appl. No. 29/530,023.
Notice of allowance dated Jun. 14, 2017 in co-pending U.S. Appl. No. 29/530,023.

* cited by examiner

STIRRED CELL AND METHOD OF USING SAME

This application claims priority of U.S. Provisional Application Ser. No. 62/114,761 filed Feb. 11, 2015, the disclosure of which is incorporation herein by reference.

FIELD

Embodiments disclosed herein relate to fluid containment pressure vessels such as stirred cells and related methods utilizing the same.

BACKGROUND

Pressure vessels for sample concentration or desalting, for example, may use air pressure as the driving force to effect separation, such as through a suitable membrane. Typically outer support housings are containment frames are necessary to contain the vessel when under pressure, hold the cover on the vessel, help prevent premature or accidental release of the cover, as well as to add strength to the assembly when pressurized. However, filtration is complete, it is often very difficult to remove the vessel from the support housing. In addition, if the vessel was attempted to be pressurized without the support housing in place, the cover would blow off.

One exemplary application of such pressure vessels are stirred cell devices. Conventional stirred cells provide pressure-based sample concentration or desalting, such as of samples containing proteins and viruses. Such devices use pressure as the driving force to force fluid through a membrane while retaining and concentrating the macromolecules too large to pass through the membrane. Typically the membrane is an ultrafiltration membrane. Desalting is achieved by a process of diafiltration where fluids are replaced and the system is re-pressurized. Conventional stirred cells can include gentle magnetic stirring to control the concentration polarization or accumulation of macromolecules on the surface of the membrane, and to minimize shear stress-induced denaturation. The devices are designed for rapid concentration or purification of macromolecular solutions, and can typically handle volumes of from 3 mls to 1000 mls.

The ultrafiltration membranes used in such stirred cells are size exclusion membranes; due to the extremely small pores, a substantial driving force is required to effect the separation. Exemplary driving forces sufficient to create high enough force to push the liquid through the membrane are centrifugation and air pressure. Air pressures of less than 75 psi are usually sufficient.

In addition to the shortcomings of such pressure vessels mentioned above, additional shortcomings specific to stirred cell devices can include the magnetic stir bar contacting and damaging the membrane; the use of non-standard connectors; fragile vent valve parts that are prone to breakage; and caps that are difficult to open and close; and possible system leakage.

It would be desirable to eliminate the containment frame, and provide appropriate venting, pressure relief, and a safety interlock in pressure vessels.

SUMMARY

The shortcomings of the prior art have been overcome by embodiments disclosed herein, which relate to a device and method for sample preparation, including purification or concentration of samples, particularly protein samples. In certain embodiments, the device is a fluid containment pressure vessel, eliminates the outer support housing present in conventional stirred cells, and provides an improved cap-to-body interface. In certain embodiments, the cap is threaded and configured to threadingly engage with the body of the stirred cell, and has sufficient structural integrity to withstand the pressures in the device without the need for a support housing. In certain embodiments, an interlock mechanism is provided that prevents the cap from being opened (e.g., removed from the body) while the device is under pressure. In certain embodiments, a pressure relief valve is provided with a pre-loaded biasing mechanism to achieve the required pressure release rate.

DETAILED DESCRIPTION

Figure 1A:
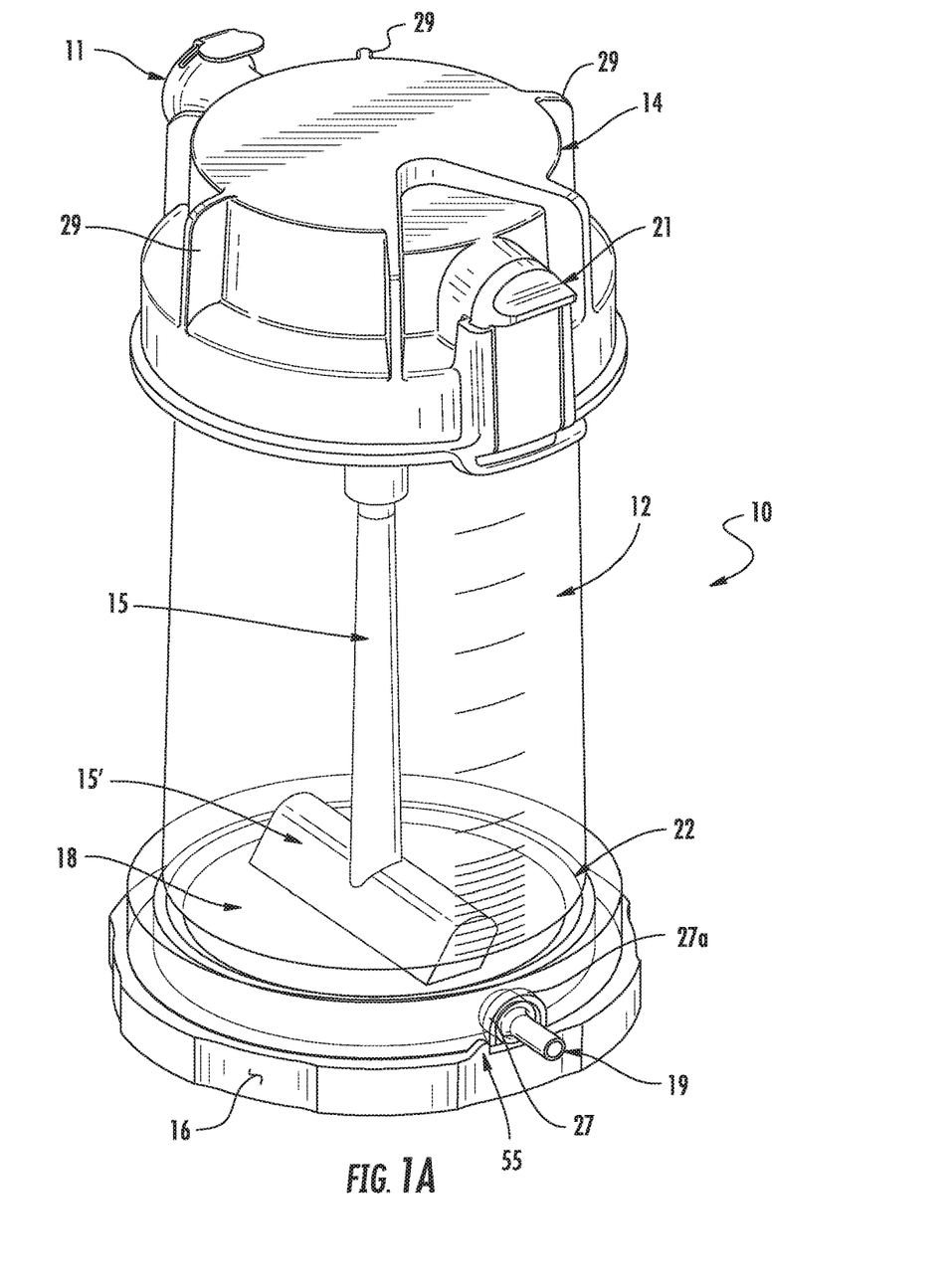
FIG. 1A is a perspective view of a stirred cell device in accordance with certain embodiments.
Figure 1B:
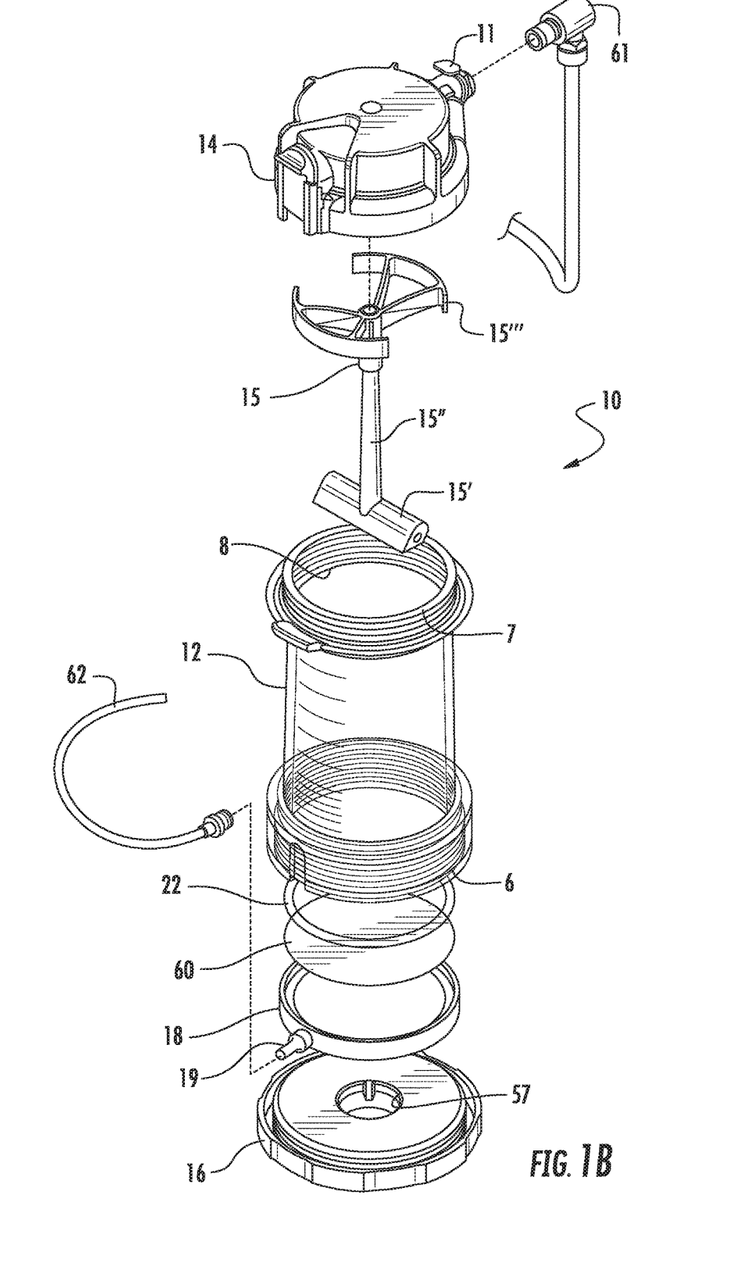
FIG. 1B is an exploded view of a stirred cell device in accordance with certain embodiments.

Turning first to FIGS. 1A and 1B, there is shown a stirred cell device 10 in accordance with certain embodiments. In certain embodiments, the stirred cell device 10 includes a body 12 that may be generally cylindrical and having an interior volume for containing the sample. Typical volumes include 50-75 ml, 200-250 mls., and 400-500 mls., although other volumes are within the scope of the embodiments disclosed herein. In certain embodiments, the body 12 can have an open bottom end that is closable by a base cap 16, and an open top end that is closable by a top cap 14. Positioned in the body 12 is a stirring mechanism for agitating the sample in the interior volume, such as a stir bar assembly 15 that includes paddle 15' that is positioned just above the membrane 60, e.g., about 1 mm above the membrane 60 surface. In certain embodiments, the paddle 15' includes an AlNiCo magnet and is magnetically actuatable. In certain embodiments, paddle 15' is part of an axial stem 15" (FIG. 1B) that is coupled to a support member 15''' that sits on a ridge 8 formed in body 12 that extends radially inwardly, In this embodiment the axial stem 15" can freely rotate within support member 15'''. In certain embodiments, the materials of construction of the body 12 are preferably thermoplastic materials, such as polysulfone and polycarbonate.

In certain embodiments, a detachable top cap 14 interfaces with the body 12 and closes the open top end of the body 12 when engaged therewith. In certain embodiments, the top cap 14 may be internally threaded and can be sealingly coupled to the body 12, such as via corresponding threads 7 on the outer surface of the top end of the body 12. Other suitable securing mechanisms include bayonets and ¼ turn threads. An annular wiper member or seal 13 (FIG. 4) may be positioned radially inwardly of the internal threads, the wiper member 13 wiping against the inside wall 12a of the top open end of the body 12 as the top cap 14 is assembled to and disassembled from the body 12. The top cap 14 may be constructed of any suitable material, such as polysulfone. In certain embodiments, the top cap 14 may include one or more quick disconnect fittings 11 (which may be valved) that can connect to suitable tubing 61 (FIG. 1B) in fluid communication with a pressure source, and that provides fluid communication to the interior of the body 12, such as via a port in the top cap 14, when the top cap 14 is coupled to the body 12 in the assembled condition. In certain embodiments, the top cap 14 has sufficient structural integrity to withstand the internal operating pressure of the device, thereby eliminating the need for an outer support housing required in conventional devices. The top cap 14 can be equipped with one or more radially outwardly extending ribs 29 to assist the user in grasping the top cap 14, which facilitates its rotation relative to the body 12.

As used herein, the term "consisting essentially of" excludes the outer support housing or containment frame required in conventional devices.

In certain embodiments, a base cap 16 interfaces with the body 12 and closes the bottom open end of the body 12 when engaged therewith. In certain embodiments, the base cap 16 is externally threaded and is coupled to the body 12 via corresponding threads on the inner surface of the bottom end of the body 12. In certain embodiments, the base cap 16 may include a base thread stop tab 55 that engages flange 27a that defines slot 27 when the base cap 16 is fully engaged with the body 12. This ensures consistent O-ring 22 compression by providing positive tactile feedback to the use that the base cap 16 is fully engaged. In certain embodiments, a membrane holder or support 18 is attached to the base cap 16 and is rotatable with respect thereto. In certain embodiments, the membrane holder 18 has a snap engagement with the base cap 16 (FIG. 7) via a plurality of axially extending members 56 (one shown) that snap into central base cap apertures 57. The snap engagement allows for relative rotation between the membrane holder 18 and the base cap 16.

Figure 7:
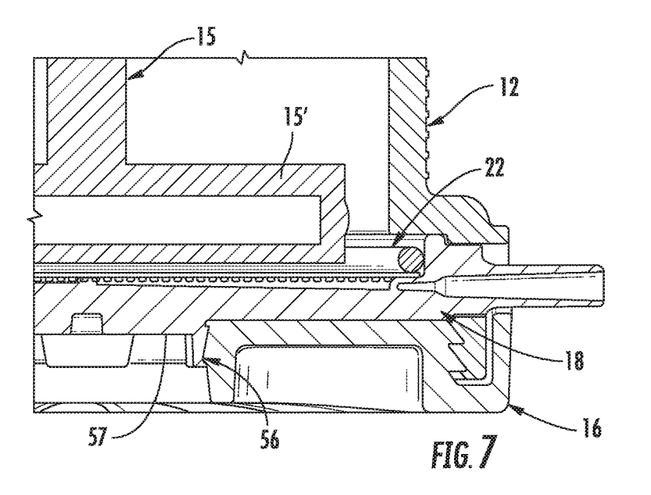
FIG. 7 is a cross-sectional view of a base cap coupled to a stirred cell body in accordance with certain embodiments.

The membrane holder 18 may include a plurality of raised projections or ribs and a channel for fluid flow to an outlet 19 (e.g., male luer slip) that may be connected to tubing 62 or the like. The plurality of projections or ribs support a membrane 60. Annular O-ring 22 may be positioned near the outer annular edge of the membrane 60 to assist in holding the membrane 60 in place and to avoid fluid leakage around the membrane 60. The outlet 19 is accommodated by a slot 27 in the body 12 when the base cap 16 is attached to the body 12. To attach the base cap 16 to the body 12, the outlet 19 is inserted into the slot 27, and the base cap 16 is rotated so that threads on the base cap 16 engage corresponding internal threads 6 on the bottom portion of the body 12. Due to the snap engagement, rotation of the base cap 16 does not force a corresponding rotation of the membrane holder 18. The base cap 16 may be constructed of any suitable material, such as polysulfone. The underside of the base cap 16 may have a concave surface to compensate for expansion deformation while the vessel is pressurized during use.

Figure 2:
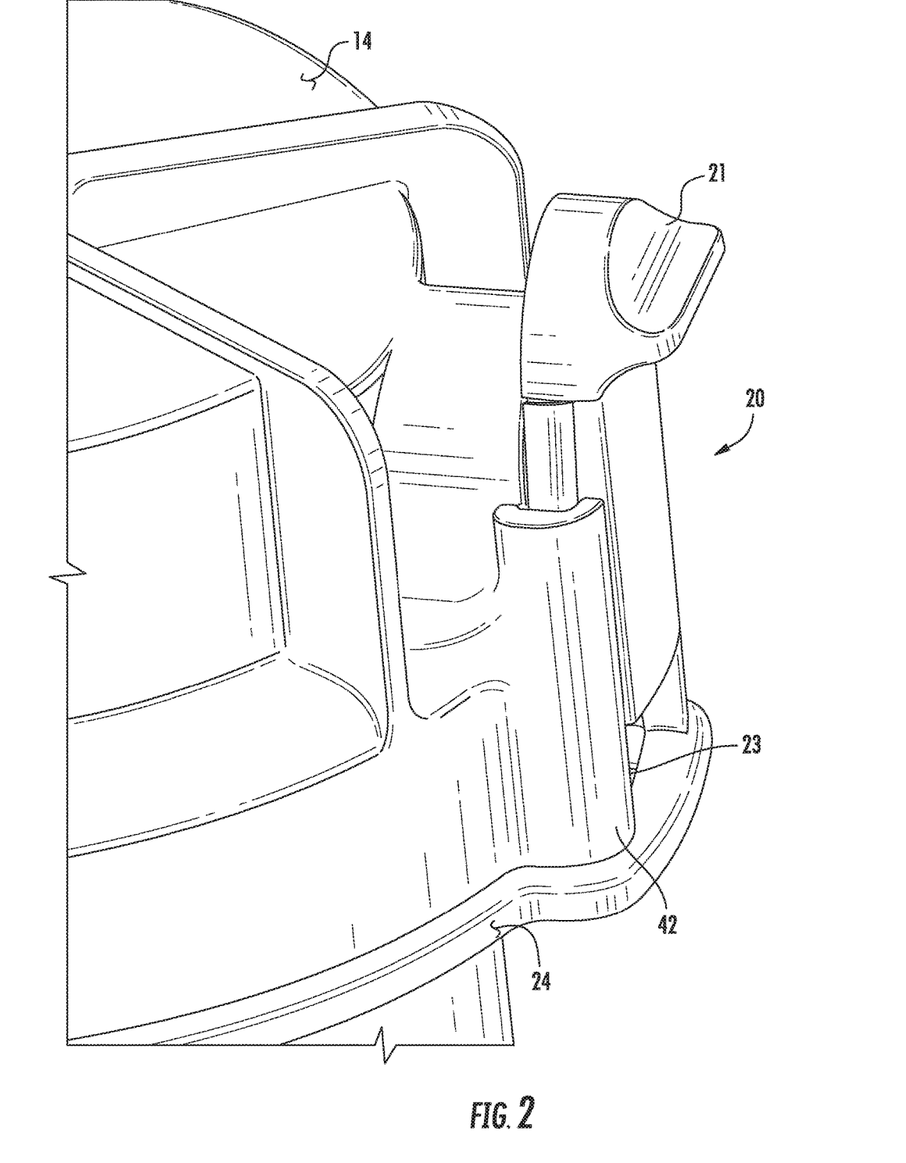
FIG. 2 is a perspective view of an interlock mechanism in an open position in accordance with certain embodiments.
Figure 3:
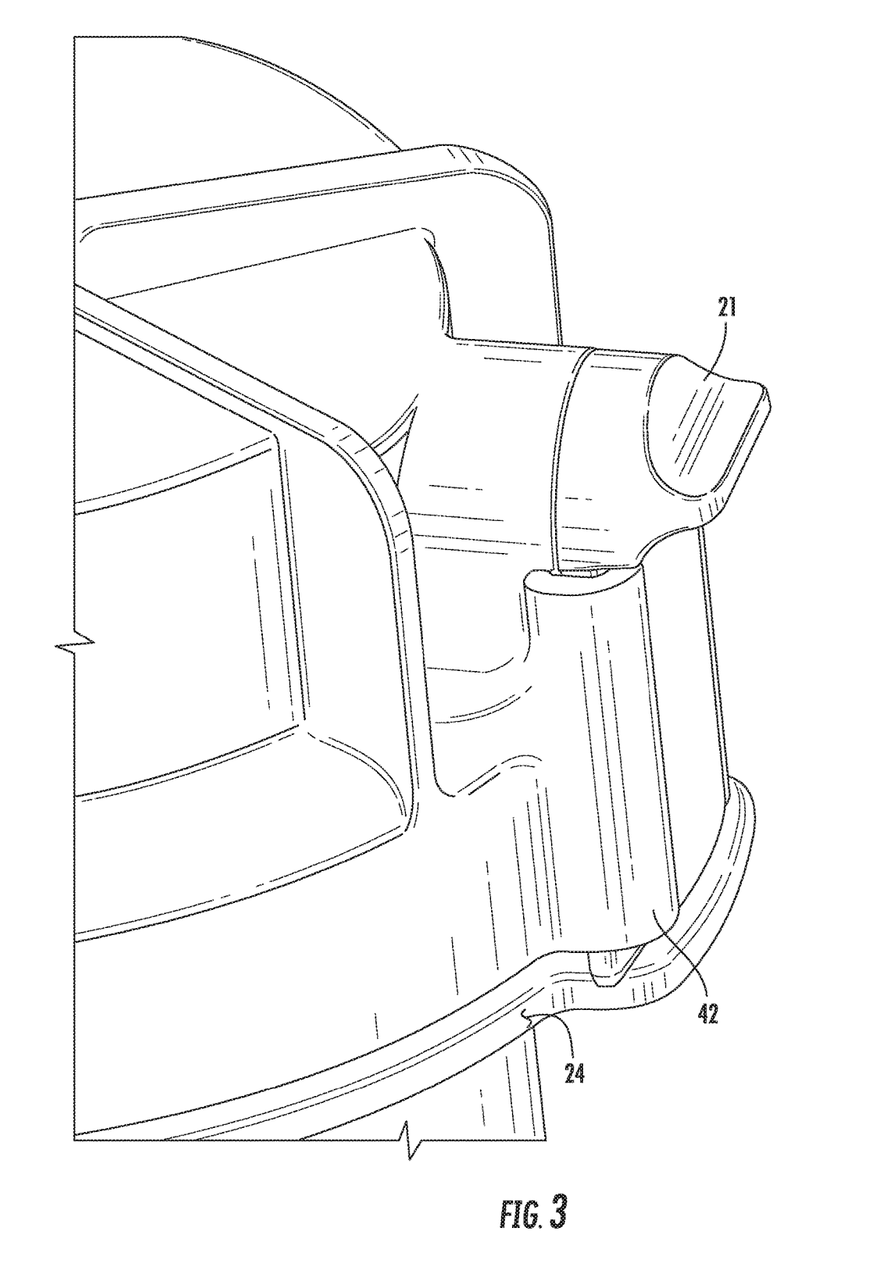
FIG. 3 is a perspective view of an interlock mechanism in a closed position in accordance with certain embodiments.
Figure 4:
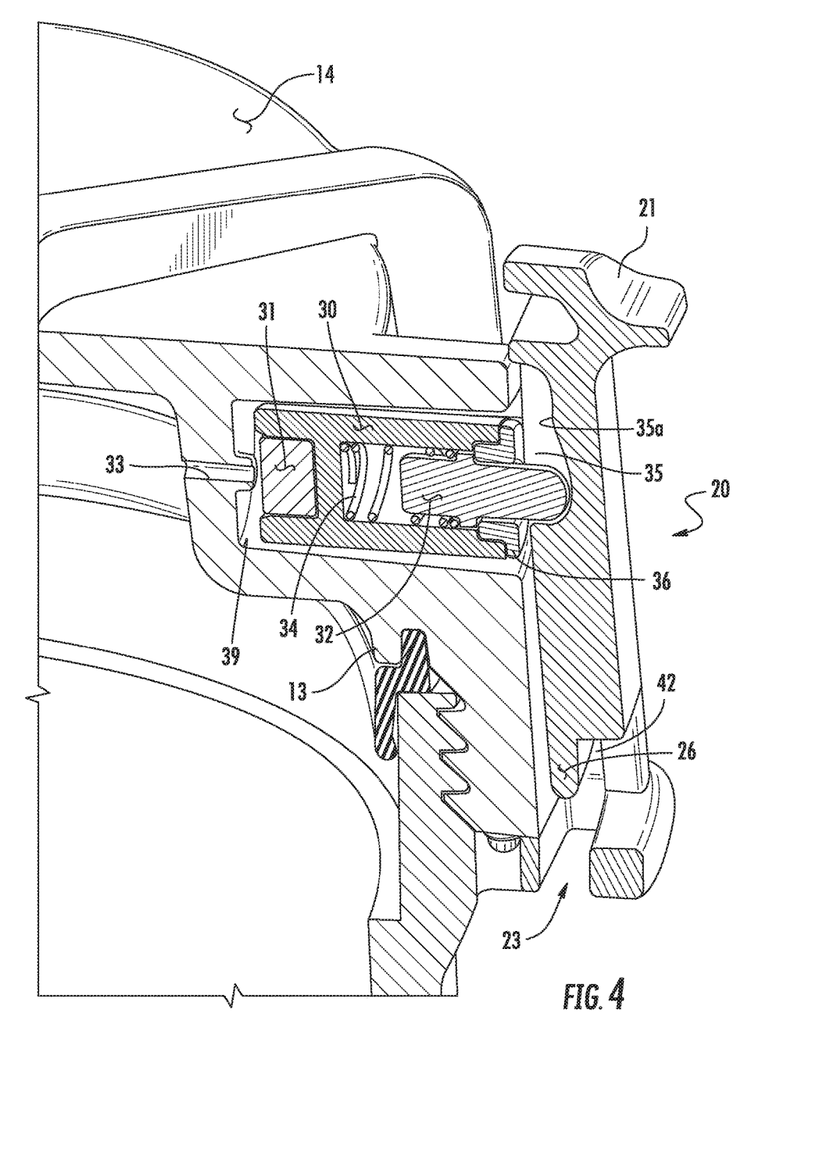
FIG. 4 is a perspective view, partially in cross-section, of an interlock mechanism and pressure relieve valve in an open position in accordance with certain embodiments.

As seen in FIGS. 2-4, in certain embodiments, the top cap 14 includes an interlock mechanism 20 to prevent opening of the top cap 14 from the body 12 while the device 10 is pressurized or during pressurization of the device 10. In certain embodiments, the interlock mechanism 20 includes a lock mechanism 21, such as a lever that is vertically slidable relative to the body 12 in track 42 of top cap 14 between an open position (FIG. 2) and a closed position (FIG. 3). When the top cap 14 is tightened on the body 12 so that it rests on annular flange 24 integral with and extending radially outwardly from the body 12, the lock mechanism 21 aligns with a lock mechanism-receiving member 23, such as a slot, in the annular flange 24. By sliding the lock mechanism 21 downwardly in track 42 so that narrow bottom extension 26 of the lock mechanism 21 enters and penetrates through the lock mechanism-receiving member 23, rotation of the top cap 14 relative to the body 12 is prevented. Those skilled in the art will appreciate that the lock mechanism-receiving member 23 need not be a slot; it could be any member or mechanism that receives the lock mechanism and prevents relative rotation between the cap 14 and the body 12.

Figure 6:
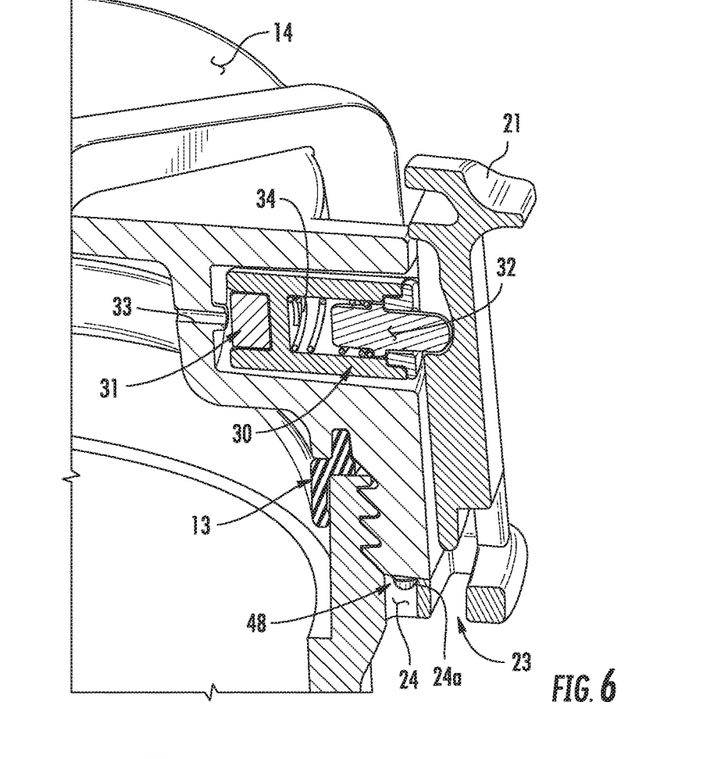
FIG. 6 is a perspective view, partially in cross-section, of an interlock mechanism and pressure relieve valve in an open position in accordance with certain embodiments.

As seen in FIG. 6, the flange 24 includes an offset or groove 24a that terminates at about the midpoint of lock mechanism-receiving member 23. The bottom annular surface of the top cap 14 includes a stop lock tab 48 that rides in groove 24a as the top cap is screwed onto the body 12 and approaches its fully tightened position. Since the groove 24a terminates at about the midpoint of the lock mechanism-receiving member 23, the stop lock tab 48 abuts against the terminal wall of the groove 24a and prevents further tightening of the top cap 14, thereby aligning the lock mechanism 21 with the lock mechanism-receiving member 23.

Figure 5:
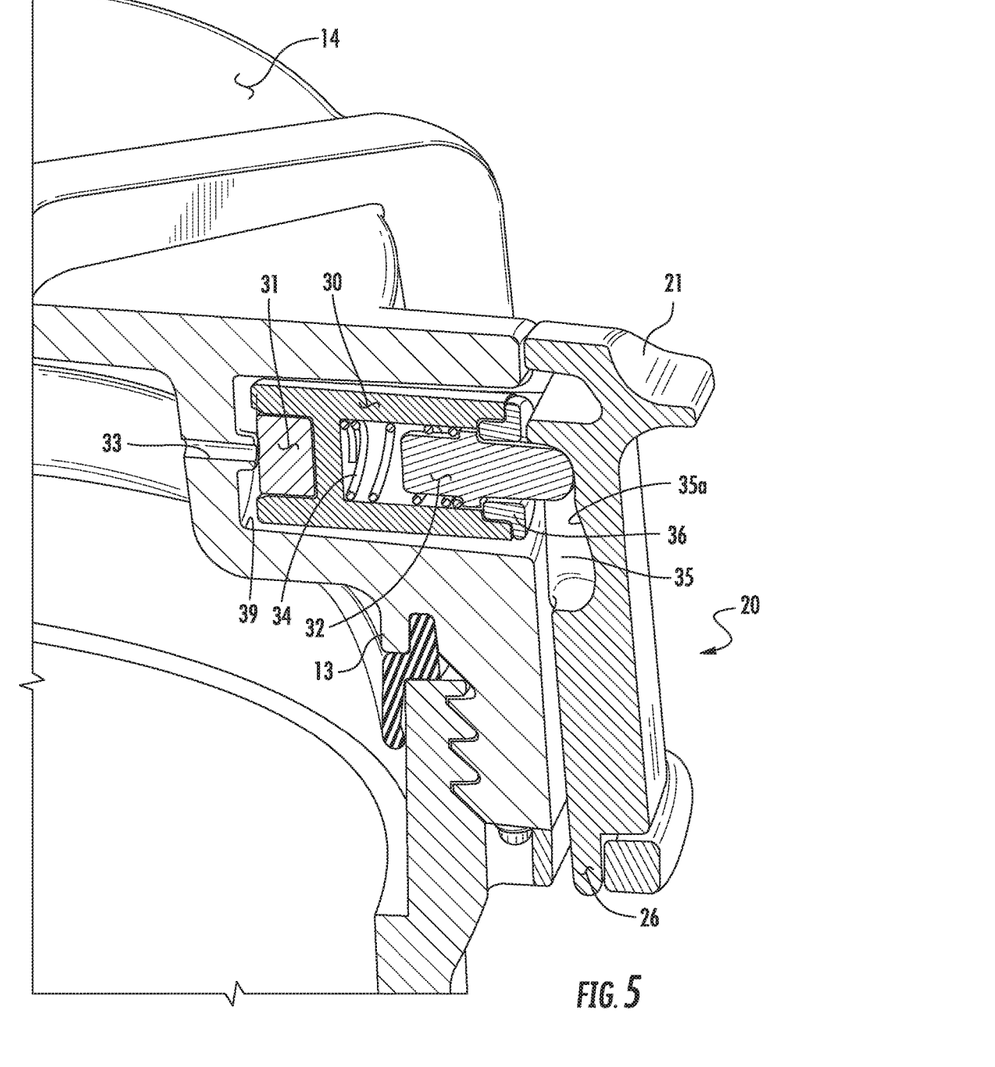
FIG. 5 is a is a perspective view, partially in cross-section, of an interlock mechanism and pressure relieve valve in a closed position in accordance with certain embodiments.

FIGS. 4 and 5 illustrate an embodiment of a pressure relief valve. In certain embodiments, the pressure relief valve has two actionable features: it provides a user actuated venting system; and it provides a pressure release vent in the event the system is over pressurized. In the embodiment shown, the pressure relief valve includes a self-contained valve cartridge or housing 30 in the top cap 14. In certain embodiments, the valve cartridge 30 is positioned radially inwardly of the interlock mechanism 20. In certain embodiments, the valve cartridge 30 includes a seal 31, such as an elastomeric seal, at one end and a compressible piston 32 at the opposite longitudinal end of the cartridge 30, the piston 32 held in place with the help of housing endcap 36. The seal 31 is positioned to seal against orifice 33 in top cap 14 that itself is positioned to provide fluid communication to the interior of the body 12 when the top cap 14 is assembled to the body 12. In certain embodiments, the orifice 33 face is offset (e.g., 0.040 inches) and the seal contact surface has a 0.015 inch full radius. The diameter of the orifice 33 controls the rate of venting of the interior volume and in certain embodiments has a 0.140 inch inside diameter. A biasing member 34, such as a uniformly wound stainless steel wire of a constant wire diameter and outside diameter biases the piston 32 radially outwardly, e.g., towards the interlock mechanism 20. In certain embodiments, the biasing member 34 has a linear spring force; for a given wire size and coil length, the more the spring is compressed, the higher the force required to further compress the spring and actuate the piston 32 thus controlling the pressure at which the system vents.

In certain embodiments, the lock mechanism 21 includes a cam slot 35. The cam slot 35 is configured and positioned so that the head of piston tracks in the cam slot 35 as the lock mechanism 21 is actuated between the fully open and fully closed positions. In certain embodiments, the lower region of the cam slot 35 extends radially outwardly to a greater extent than the upper region of the cam slot 35, with a transitioning ramp 35a between these lower and upper regions. Accordingly, when the lock mechanism 21 is in the open position as shown in FIG. 4, the piston 32 is positioned in the lowest region of the cam slot 35, and thus the piston 32 is biased radially outwardly to its furthest extent. In this open position, fluid (e.g., air) within the body 12 can vent through orifice 33, into the cavity 39 holding valve cartridge 30, around the small gap between the valve cartridge 30 and the walls of the cavity 39, and out of the device. In certain embodiments, the stroke to close the valve and set the biasing member 34 can be designed to cause the piston to move from between 0.030 inches to 0.050 inches, preferably about 0.040 inches, by appropriately configuring the cam slot 35. In certain embodiments, the valve is designed to open (e.g., the force of the biasing member 34 is overcome by the pressure acting on the pressurized area of the elastomeric seal 31) at a pressure range of 85 psi to 105 psi. This is a function of the size of the orifice 33 opening and the biasing member spring rate and spring compression.

As the lock mechanism 21 is actuated towards the closed position, the piston tracks in the cam slot and is forced radially inwardly against the force of the biasing member 34, forcing the seal 31 into sealing contact with the orifice 33 and thus preventing fluid from venting from the body 12 through the orifice 33. The cam slot 35 compresses the cartridge 30 to engage contact between the seal 31 and the orifice 33 and compresses the piston 32 and biasing member 34 to achieve the final pressure release value.

In certain embodiments, the biasing member 34 is pre-loaded (e.g., 60%) to achieve the required release rate with maximum travel of the piston 32.

Figure 8A:
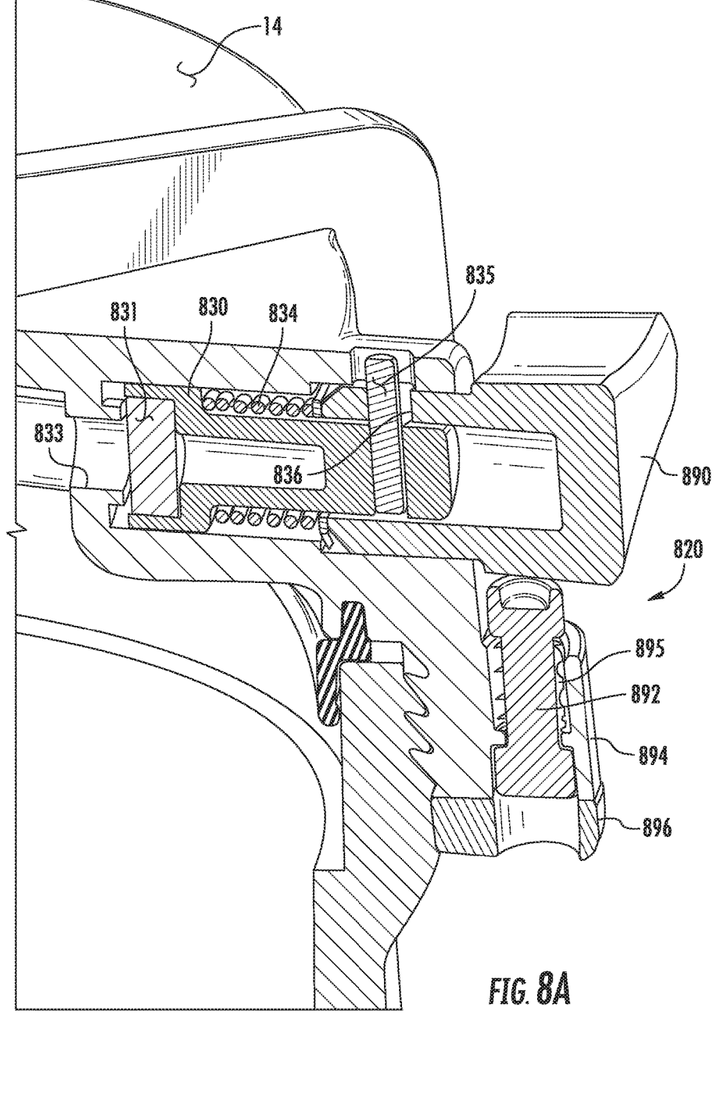
FIG. 8A is a perspective view, partially in cross-section, of an interlock mechanism and pressure relieve valve in an open position in accordance with certain embodiments.
Figure 8B:
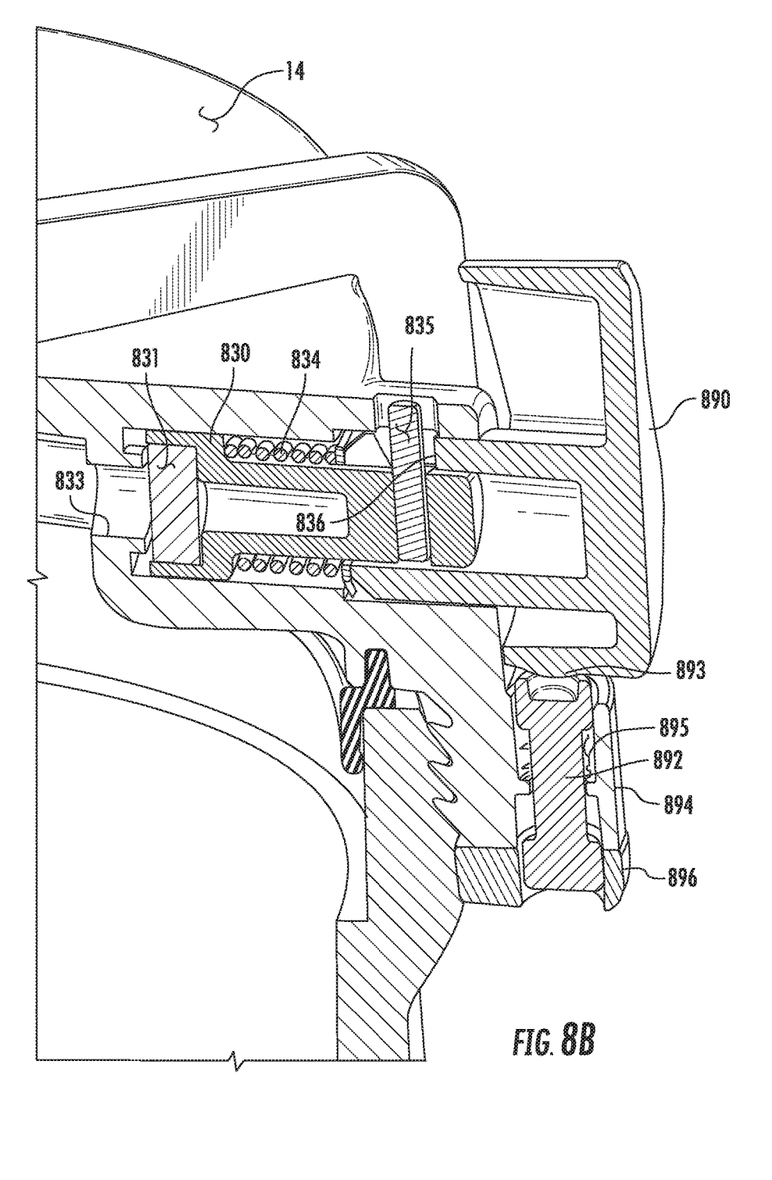
FIG. 8B is a perspective view, partially in cross-section, of an interlock mechanism and pressure relieve valve in a closed position in accordance with certain embodiments.

An alternative embodiment of a valve and lock system is shown in FIGS. 8A and 8B. In the embodiment shown, the pressure relief valve includes a valve in the top cap 14. In certain embodiments, the valve is positioned radially inwardly of the interlock mechanism 820. In certain embodiments, the valve includes a valve shaft 830 having a seal member 831 at one end. The valve shaft 830 is anchored in place (not free-floating) inside the cap 14 in a normally closed position, compressing a biasing member 834 to a pre-determined load. This results in an applied force to seal the valve shaft 830, and in particular, the seal member 831, against the orifice 833 in the cap 14, that itself is positioned to provide fluid communication to the interior of the body 12 when the top cap 14 is assembled to the body 12. The valve shaft 830 is connected to the rotary handle 890 via a linking member 835 which allows the handle 890 to rotate and pull the valve shaft 830 into an open position, releasing the seal 831 from the orifice 833. In certain embodiments, the linking member 835 is a pin inserted into the valve shaft 830 through a cam slot 836 in the handle 890. In certain embodiments, the biasing member 834 has a linear spring force; for a given wire size and coil length, the more the spring is compressed, the higher the force required to further compress the spring. As the lock mechanism is actuated towards the closed position, the valve cartridge is forced radially inwardly against the force of the biasing member 834, forcing the seal 831 into sealing contact with the orifice 833 and thus preventing fluid from venting from the body 12 through the orifice 833.

In certain embodiments, the interlock mechanism 820 includes pin 892. The pin 892 is positioned in a radial housing 894 of the top cap 14, and spring loaded via biasing member 895. The rotatable handle 890 includes a raised boss 893 (FIG. 8B) on the lower extremity which engages the spring loaded pin 892 when the handle 890 is actuated to the closed position. This cause the pin 892 to move axially and enter the region defined by radial housing portion 896 of the body 12. Since portions of the pin 892 now occupy the interior of the radial housing 894 of the cap 14 and the radial housing 896 of the body 12, the cap 14 cannot be rotated with respect to the body 12, and it is locked in the closed position during pressurization.

In operation in certain embodiments, the system is vented when the handle 890 is in the open position, as shown in FIG. 8A. In this position the cam slot 836 in the handle applies a lateral force to the attachment pin 835 between the shaft 830 and the handle 890 further compressing the pre-loaded spring 834 (there is a small gap between the orifice 833 and the seal 831 in this position). In this position, a gap between the handle 890 and the pin 835 allows the pin 892 to auto disengage from the corresponding geometry on the upper region of the body 12 (facilitated by a pre-loaded spring mechanism 895). When the handle is rotated back 90 degrees as shown in FIG. 8B, the pin 835 connecting the valve shaft 830 to the handle 890 is released and allows the compressed spring 834 to force the valve shaft 830 radially inwardly, thus applying a force to the seal 831 against the orifice 833. When handle 890 is rotated to the closed position, the raised geometry 893 on the lower extremity of the handle 890 engages the locking pin 892 and forces the pin 892 into the corresponding opening defined by housing 896 on the body 12. When In the closed position, there is clearance between the cam slot 836 in the handle 890 and the connecting pin 835 in the valve shaft 830, if the system is over pressurized the pressure/force in the vessel will overcome the spring force and move the seal 831 and shaft 830 to open.

In certain embodiments, the valve is designed to open (e.g., the force of the biasing member 834 is overcome by the pressure acting on the pressurized area of the elastomeric seal 831) at a pressure range of 85 psi to 105 psi. This is a function of the size of the orifice 833 opening and the biasing member spring rate and spring compression.

In certain embodiments, the biasing member 834 is pre-loaded (e.g., 60%) to achieve the required release rate with maximum travel of shaft 830.

Figure 9A:
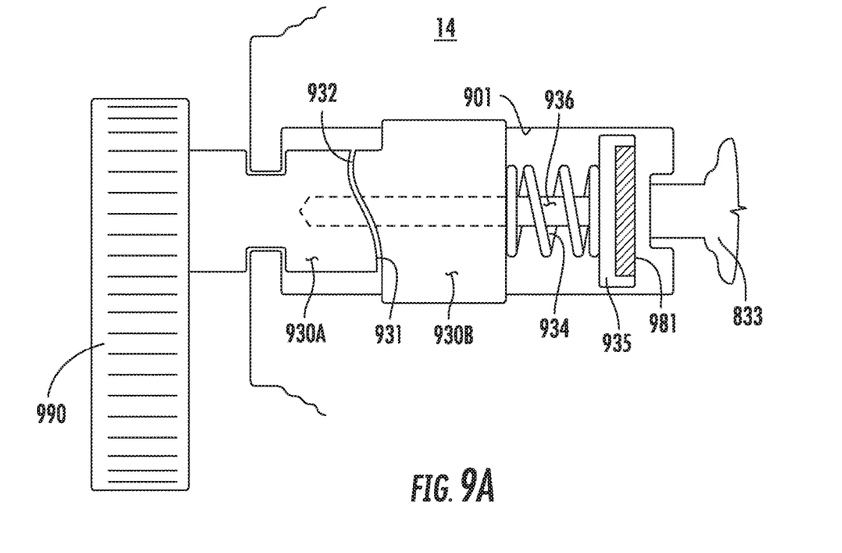
FIG. 9A is a cross-sectional view of a vent valve mechanism in an open position in accordance with certain embodiments.
Figure 9B:
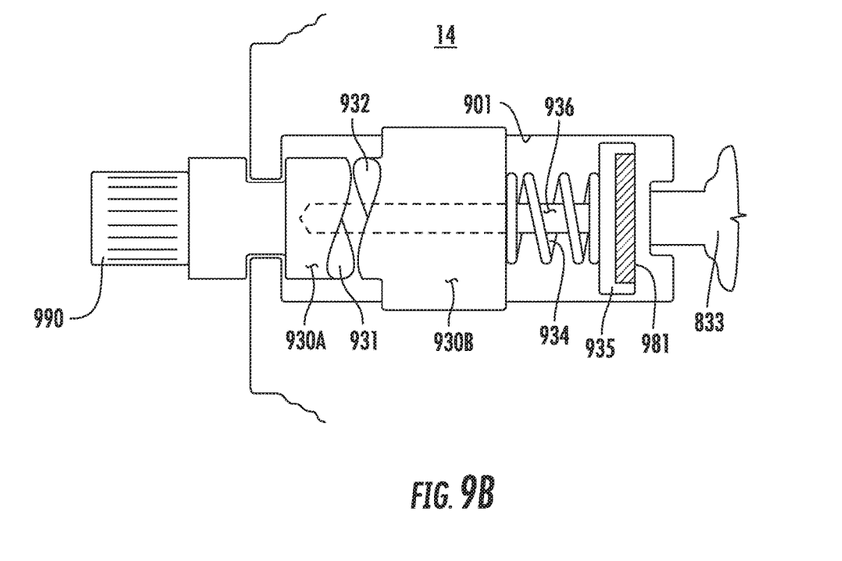
FIG. 9B is a cross-sectional view of a vent valve mechanism in a closed position in accordance with certain embodiments.

FIGS. 9A and 9B illustrate an embodiment of a vent valve mechanism. In the embodiment shown, the region of the cap 14 that houses the valve includes a cavity region 901. The valve stem is a two-component mechanism; in certain embodiments it includes a first valve stem member 930A of round or cylindrical cross-section, and a second valve stem member 930B of square cross-section, positioned radially inwardly of the first member 930A. In certain embodiments, the valve stem first member 930A is rotatable within cavity 901 about pin 936, such as by actuation of handle 990, but is not movable radially within the cavity 901. The first member 930A has a shaped end face 931 that is configured to mate with a corresponding shaped front face 932 of the valve stem second member 930B when the valve is in the open position as shown in FIG. 9A. In this configuration, the combined length of the valve stem members 930A and 930B is at a minimum. The shapes of the end face 931 and front face 932 are not particularly limited, provided they are shaped to engage in one position to define a first stem length, and disengage in another position to define a second stem length greater than the first stem length. The valve stem second member 930B can move radially within the cap 14 (e.g., along pin 936), but cannot rotate within the cavity region 901 due to the relative geometries of the cavity and the second member 930B. The handle 990 is rotatable, but does not move radially. A biasing member 934 is positioned about pin 936 between the end face of the valve stem second member 930B and the distal end 935 of the valve as shown.

The system is vented when the handle 990 is in the open position, as shown in FIG. 9A, and there is thus a small gap between the orifice 833 and the seal 981 in this position. When the handle 990 is rotated (e.g., 90 degrees), the shaped end face 931 of the valve stem first member 930A is moved out of mating alignment with the front face 932 of the second member 930B, thereby forcing the non-rotating valve stem second member 930B to move radially inwardly, towards the orifice 833, against the bias of the biasing member 934, as seen in FIG. 9B. The valve stem second member 930B compresses the biasing member 934, which in turn applies a force to the seal 981 against the orifice 833. Reversing the handle 990 vents the system. If the system is over pressurized, the pressure/force in the vessel will overcome the spring force of the biasing member 934 and move the valve to the open position.

In certain embodiments, the device may be assembled by snapping the membrane holder 18 onto the base cap 16, and assembling the membrane coupon 60 onto the membrane holder 18 and retaining it with O-ring 22. The membrane holder 18 then may be positioned with the luer outlet 19 aligned with the opening or slot 27 in the body 12, and the base cap 16 may be tightened onto the body 12 by engaging the respective threads 6 in the base cap 16 and the body 12. The device is now ready to receive sample, which can be introduced by any suitable mechanism to the interior volume of the body 12. The stir bar assembly 15 is positioned in place by resting the support member 15''' on the shelf created by the radially inwardly projecting ridge 8 in the body 12. The top cap 14 is then engaged with the body 12 and tightened. The lock mechanism 21 is actuated to the closed position to lock the top cap 14 in place and load the pressure relief valve. A filtrate tube may be attached to the luer outlet 19, which can drain into a suitable filtrate container. A pressure source is placed in communication with the quick disconnect fitting 11 on the top cap 14. The device is positioned on a stir plate, the stir plate is turned on to actuate the stir bar assembly 15, and pressure is applied via the pressure source to begin filtration.

In certain embodiments, the filtration run is typically monitored until the sample is concentrated to the required degree, such as 10×. When concentration is complete, the pressure source is disconnected, and the lock mechanism 21 is raised to the open position to disengage it with the lock mechanism-receiving member 23, depressurizing the interior volume of the body 12 via the pressure relief valve by allowing air to vent through now unsealed orifice 33. Once the cell is depressurized, the top cap 14 can be removed to provide access to the concentrated sample. The concentrated sample on the membrane can be recovered such as with a pipettor. The device may be cleaned and re-used.

What is claimed is:

1. A fluid containment pressure vessel adapted to be in communication with a pressure source, comprising:
    (a) a body having an interior volume;
    (b) a cap sealingly attachable to said body, said cap having an orifice that communicates with said interior volume when said cap is attached to said body; and
    (d) a pressure relief valve actuatable between an open position allowing fluid to flow from said interior volume through said orifice in said cap, and a closed position preventing fluid from flowing from said interior volume through said orifice; wherein said pressure relief valve is operatively connected to a lock mechanism such that removal of said cap from said body is prevented when said pressure relief valve is in said closed position.

2. The fluid containment pressure vessel of claim 1, wherein said pressure relief valve is positioned in said cap.

3. The fluid containment pressure vessel of claim 1, wherein said lock mechanism comprises a lever movable on said cap to engage with a lock-receiving member on said body.

4. The fluid containment pressure vessel of claim 1, wherein said pressure relief valve comprises a seal, a piston and a biasing member biasing said piston to a valve open position, and wherein said lock mechanism comprises a cam slot in which said piston tracks such that actuation of said lock mechanism from a first position to a second position forces said piston to overcome the force of said biasing member and cause said seal to seal against said orifice.

5. The fluid containment pressure vessel of claim 1, wherein the lock mechanism comprises a lever which locks said cap with the body.

6. The fluid containment pressure vessel of claim 1, wherein the lock mechanism comprises a pin actuatable to a position where it prevents rotation of said cap relative to said body.

7. The fluid containment vessel of claim 1, further comprising a stir bar assembly in said interior volume.

8. The fluid containment vessel of claim 1, wherein said interior volume comprises a membrane.

9. The fluid containment vessel of claim 8, further comprising a base cap sealingly attachable to said body, and a membrane holder rotatingly coupled to said base cap.

10. A method of filtering a sample, comprising:
    providing a pressure vessel comprising a body having an interior volume, a membrane positioned in said interior volume, a stir member positioned in said interior volume, a cap sealingly attachable to said body, said cap having an orifice in communication with said interior volume, and a pressure relief valve actuatable between an open position allowing fluid flow from said interior volume through said orifice in said cap, and a closed position preventing fluid from flowing from said interior volume through said orifice, said pressure relief valve being operatively connected to a lock mechanism for preventing removal of said cap from said body when said pressure relief valve is in said closed position;
    introducing said sample into said interior volume;
    sealing said cap to said body;
    actuating said pressure relief valve to said closed position with said lock mechanism;
    applying pressure as to said interior volume to filter said sample with said membrane;
    stirring said sample with said stir member;
    ceasing the application of pressure to said interior volume;
    venting said interior volume by actuating said pressure relief valve to said open position with said lock mechanism;

removing said cap from said body to access said interior volume; and recovering product retained on said membrane.

11. The method of claim 10, wherein said pressure relief valve comprises a seal, a piston and a biasing member biasing said piston to a valve open position, and wherein said lock mechanism comprises a cam slot in which said piston tracks such that actuation of said lock mechanism from a first position to a second position forces said piston to overcome the force of said biasing member and cause said seal to seal against said orifice.

* * * * *

UNITED STATES PATENT AND TRADEMARK OFFICE
CERTIFICATE OF CORRECTION

| | | |
|---|---|---|
| PATENT NO. | : 10,088,398 B2 | Page 1 of 1 |
| APPLICATION NO. | : 14/994402 | |
| DATED | : October 2, 2018 | |
| INVENTOR(S) | : Clark et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 252 days.

Signed and Sealed this
Twenty-third Day of April, 2019

Andrei Iancu
*Director of the United States Patent and Trademark Office*